(12) United States Patent
Trovato

(10) Patent No.: US 8,741,267 B1
(45) Date of Patent: Jun. 3, 2014

(54) METHOD FOR TREATING PERIODONTAL DISEASE

(76) Inventor: Joseph P. Trovato, Allentown, NJ (US)

( * ) Notice: Subject to any disclaimer, the term of this patent is extended or adjusted under 35 U.S.C. 154(b) by 28 days.

(21) Appl. No.: 12/459,127

(22) Filed: Jun. 26, 2009

(51) Int. Cl.
*A61K 8/00* (2006.01)

(52) U.S. Cl.
USPC .......................................... 424/49; 514/900

(58) Field of Classification Search
None
See application file for complete search history.

(56) References Cited

U.S. PATENT DOCUMENTS

| | | | |
|---|---|---|---|
| 4,329,333 A | 5/1982 | Barr | |
| 4,460,642 A | 7/1984 | Errede et al. | |
| 4,521,403 A * | 6/1985 | Simon et al. | 424/51 |
| 4,569,837 A | 2/1986 | Suzuki et al. | |
| 4,582,052 A | 4/1986 | Dunn et al. | |
| 4,592,489 A | 6/1986 | Simon et al. | |
| 5,057,497 A | 10/1991 | Calam et al. | |
| 5,137,718 A | 8/1992 | Gillespie | |
| 5,438,076 A | 8/1995 | Friedman et al. | |
| 5,503,847 A | 4/1996 | Queen et al. | |
| 5,578,315 A | 11/1996 | Chien et al. | |
| 5,639,476 A * | 6/1997 | Oshlack et al. | 424/468 |
| 5,776,494 A | 7/1998 | Guskey et al. | |
| 5,843,408 A | 12/1998 | Hattori et al. | |
| 5,916,882 A | 6/1999 | Jeng | |
| 5,998,528 A | 12/1999 | Tsipursky et al. | |
| 6,126,444 A * | 10/2000 | Horiguchi | 433/216 |
| 6,197,331 B1 | 3/2001 | Lerner et al. | |
| 6,228,354 B1 | 5/2001 | Jeng | |
| 6,290,984 B1 | 9/2001 | Tapolsky et al. | |
| 6,689,339 B1 * | 2/2004 | Tanaka et al. | 424/44 |
| 6,692,757 B1 * | 2/2004 | Day et al. | 424/406 |
| 7,538,082 B2 * | 5/2009 | Podolsky | 514/1.1 |
| 7,955,616 B2 * | 6/2011 | Kronenthal | 424/426 |
| 2002/0004065 A1 | 1/2002 | Kanios | |
| 2003/0049320 A1 | 3/2003 | Bhagwatwar et al. | |
| 2003/0198673 A1 * | 10/2003 | Oshlack et al. | 424/468 |
| 2005/0058744 A1 * | 3/2005 | Steinberg et al. | 426/3 |
| 2005/0191270 A1 * | 9/2005 | Gruening et al. | 424/78.3 |
| 2008/0063681 A1 * | 3/2008 | Simon et al. | 424/423 |
| 2008/0147197 A1 * | 6/2008 | McKay | 623/23.51 |

OTHER PUBLICATIONS

American Dental Association, "Periodontal Diseases: Preventing Tooth Loss." 2003. No. W121.

* cited by examiner

*Primary Examiner* — Frederick Krass
*Assistant Examiner* — Dennis J Parad
(74) *Attorney, Agent, or Firm* — Bruzga & Associates; Charles E. Bruzga; Jay S. Pattumudi

(57) ABSTRACT

A periodontal medicament composition comprising povidone iodine, an agar carrier, and optionally a bio-compatible, radio-opaque salt, for treating periodontal disease is disclosed, along with a method for preparing the same. A method is also disclosed for delivering the periodontal medicament composition, while in a liquid state, into the periodontal pocket of a patient afflicted with periodontitis whereupon due to the unique properties of the agar carrier, it solidifies to the contours of the periodontal pocket to form a periodontal medicament implant for releasing the povidone iodine over a period of time. In addition, a prepackaged periodontal medicament delivery system for treating the periodontal disease is disclosed which comprises (i) a tubular dispensing apparatus for retaining and storing one or more treatment units of the periodontal medicament composition in a solid state, and for delivery of the composition after conversion to a liquid state to the periodontal pocket of a patient afflicted with the periodontal disease; and (ii) a funnel-shaped tubular device adapted for coupling with the dispensing apparatus to facilitate the delivery of the periodontal medicament composition into the periodontal pocket. For storage and shipping or transport, the tubular dispensing apparatus and funnel-shaped tubular device are packaged in a light-resistant container.

13 Claims, 3 Drawing Sheets

METHOD FOR TREATING PERIODONTAL DISEASE

FIELD OF THE INVENTION

The present invention relates to a composition and method for treating periodontal disease by placing a carrier containing a compatible and suitable periodontal medicament into the periodontal pocket of a patient. More particularly, the carrier is designed to release the periodontal medicament, specifically periodone iodine, over a sustained period of time for treating the periodontal disease.

BACKGROUND OF THE INVENTION

Periodontal disease can have serious consequences to human health. Briefly, periodontal disease is characterized by the loss of the connective tissue structures and bone below the gum line. It typically results in the formation of a so-called periodontal pocket exceeding about 3 mm in depth, and inflammation. It is caused by the accumulation of bacteria and other microbes in the crevice (sulcus) between the gum and a tooth, and usually occurs after the onset of gingivitis.

The disease of periodontitis can cause the tissues connecting the gum to the teeth to deteriorate, resulting in the loss of supporting attachment to the associated tooth and subsequent tooth loss, often times accompanied by halitosis. In addition to these localized effects, medical studies have found an association between periodontal disease and adverse effects in other parts of the body, such as cardiovascular disease, diabetes, and premature births. A strong need therefore exists to provide an effective treatment to eradicate (kill) the bacteria and other microbes that cause periodontal disease.

Three approaches for treating periodontal disease have included (A) the time-released application of an antibiotic, (B) the time-released application of chlorahexadine, an antimicrobial agent, and (C) lavaging with a solution containing an antibacterial agent such as povidone iodine. Each of these approaches suffers serious drawbacks as the following shows.

A. Antibiotics

Antibiotics are antimicrobial agents that are derived from living organisms, such as bacteria or fungus. Typical antibiotics selectively kill only certain types of bacteria, and not other types. Thus, an antibiotic might not kill all the types of malignant bacteria that cause periodontal disease, thereby impairing its effectiveness. Secondly, bacteria may become resistant to the antibiotic, further impairing its effectiveness. With these serious drawbacks in mind, two antibiotic products that have been sold in the US are described.

An ATRIDOX® pharmaceutical delivery system comprises a time-released antibiotic, doxycycline contained in a liquid carrier that is injected into the periodontal pocket. The carrier solidifies so that it can remain in the periodontal pocket for a sustained duration, and allows the release of doxycycline over a sustained period of time, typically over a period of 3-4 days. The liquid carrier is prepared from a two-component mixture. Once solidified, the carrier cannot again be liquefied and reused, so that each time a patient is treated, a new batch of carrier must be prepared. Additionally, the antibiotics used suffer the drawbacks described above.

An ARESTIN® medication-dispensing device uses the antibiotic minocycline that is prepared in the form of a powder. It is inserted into the periodontal pocket with a carpule which is a tube-like device having a plunger. The powdered antibiotic dissolves over time to kill bacteria, but often does not remain localized in the periodontal pocket. This reduces its effectiveness to the disease in the pocket. The antibiotic also suffers from the drawbacks described above.

B. Chlorahexadine—Antimicrobial Agent

The PERIO CHIP™ sustained release polymer device comprises a small, gelatin-based carrier and medicament of the anti-microbial agent chlorahexadine in the form of a wafer. The wafer is inserted into the periodontal pocket, and dissolves over a small period of time so as to release chlorahexadine. One drawback to using chlorahexadine is that its antimicrobial action is inhibited by the presence of blood. Because bleeding is common in a diseased periodontal pocket, the effectiveness of chlorahexadine is diminished. Another disadvantage of using the PERIO CHIP™ is that it uses gelatin as a carrier for the anti-microbial agent. The "chip" must be kept refrigerated when not in use because when it is inserted into the periodontal pocket of the patient, it will begin to dissolve at the internal temperature of the patient's mouth. As such, the gelatinized "chip" won't be sustained within the pocket for a length of time, usually less than 24 hours, that will enable the active ingredient to completely treat the diseased pocket. An inefficiency therefore accompanies this approach since multiple "chip" treatments are required.

C. Povidone Iodine—Antibacterial Agent

The medicament povidone iodine is effective on a broad spectrum of bacteria, and does not appear to cause the formation of strain-resistant bacteria as do antibiotics. It is also non-staining to the teeth. It is effectively used for short-term treatments, and its antibacterial action is not inhibited by the presence of blood. Typically, a dentist will prepare an aqueous solution of povidone iodine to lavage, or wash, the periodontal pocket.

However, owing to the liquid nature of the solution containing the povidone iodine, the solution quickly drains from the periodontal pocket. This compels a dentist to apply a considerable quantity of solution (e.g., 20 cc's) in a single visit by the patient. The procedure typically takes approximately 2-3 minutes. Unfortunately, the administration of a considerable quantity of solution incurs the risk of the patient inadvertently swallowing the povidone iodine solution. The drawback of this approach is that it can harm the patient since the ingestion of too much povidone iodine can cause toxic reaction in the body. For instance, the thyroid gland can become abnormally enlarged, causing the gland to produce too much thyroid hormone, which in turn, can cause adverse affects throughout the body, and in severe reactions, death. Other toxic effects include swelling of the throat or stomach, swelling or paralysis of the esophagus, and asphyxiation from swelling of the larynx.

As indicated above, the lavaging procedure using a povidone iodine solution takes approximately 2 to 3 minutes during which time the liquid solution will quickly drain from the periodontal pocket. In order to make the administration of the povidone iodine effective, a dentist will use it in a relatively high concentration of the solution, e.g., 10% by volume. Such a high concentration exacerbates the problem and risk of a patient inadvertently ingesting the solution.

Accordingly, it is desirable to provide a composition and method for effectively delivering a medicament, such as povidone iodine, to the periodontal pocket over a period of time, i.e., for a minimum time of treatment of 24 hours, preferably 1 to 3 days, in order to bring about the result of (i) effectively and substantially eliminating bacteria in the periodontal pocket that causes the periodontal disease as well as decreasing microbial flora; (ii) reducing the size of the periodontal pocket caused by the periodontal infection; (iii) retaining and increasing attachment of the affected gum(s) to the tooth or teeth, as the case may be; (iv) decreasing accompanying bleeding; and (v) substantially avoiding toxic reaction in the body due to inadvertent ingestion of the medicament by the patient over a short period of time.

These and other objects are accomplished by various embodiments of the invention which are described in detail as follows.

SUMMARY OF THE INVENTION

The invention provides a periodontal medicament composition for treating periodontal disease comprising (a) from 0.2 to 12.0 percent, preferably from 5 to 10 percent, agar; (b) from 1.25 to 10 percent, preferably from 2 to 5 percent, povidone iodine; and optionally, up to 3 percent of a bio-compatible, radio-opaque salt that is opaque to X-rays or which can render the composition opaque. The percentages expressed are based on the total volume of the composition. The composition is characterized in that it is in a substantially solid state at a temperature below 100° F. One of the main benefits of the periodontal composition according to the invention is that the composition is in a solid state at room temperature and can be converted to a liquid state by heating it to at least 180° F. preferably from 180° F. to 200° F., for at least two minutes, preferably for at least 6 minutes, and thereafter lowering the liquid state composition to a patient-receptive temperature range of from 110° F. to 149° F., preferably from 110° F. to 140° F., for transport into the periodontal pocket of a patient afflicted with periodontal disease. Once injected into the periodontal pocket, the composition will congeal into a substantially solid state form that will take the shape of the periodontal pocket. This results in a periodontal medicament implant for the release of the povidone iodine into the pocket over a sustained period of time for treating the periodontal disease.

The optional presence of the bio-compatible, radio-opaque salt provides a visualization of the placement of the periodontal medicament composition in the periodontal pocket when X-rays are taken of the affected region of the mouth. When present, the bio-compatible, radio-opaque salt preferably comprises from 0.1 to 1 percent of the composition based on the composition's total volume. Examples of the radio-opaque salt suitable for the periodontal composition include a non-toxic salt or oxide of a heavy metal atom, and more specifically, barium sulfate, barium sulfate monomer, tin methacrylate monomer, zirconium dioxide, bismuth trioxide, bismuth subcarbonate, zirconium dioxide, or tungsten.

In another aspect of the invention, a method for the preparation of a periodontal medicament composition is provided which comprises the steps of (a) heating an aqueous solution of from 0.2 to 12.0 percent agar to a temperature of at least 180° F., preferably from 180 to 200° F.; (b) adding from 1.25 to 10.0 percent povidone iodine to the agar solution to form an agar/povidone iodine liquid solution; (c) optionally adding up to 3 percent of a bio-compatible radio-opaque salt that is opaque to X-rays or which can render the composition opaque, to the liquid solution; (d) maintaining the temperature of the liquid solution above 180° F. for at least two minutes, preferably for at least six minutes; and (e) sufficiently lowering the temperature of the liquid solution, preferably to room temperature, for transforming the solution into a solid state periodontal medicament composition for treating periodontal disease. The percentages expressed are based on the total volume of the composition. In addition, preferences for the concentration ranges of the composition are the same as those stated for the preparation of the periodontal medicament composition itself as described above.

In addition, one or more treatment units for treating periodontal disease is provided. A treatment unit will comprise anywhere from 1 to 5 cc's of the periodontal medicament composition described above. The treatment unit(s) is in a substantially solid state at a temperature below 100° F.

Once the periodontal composition is prepared and stored at room temperature, the solid state composition can be prepared for administration to a patient for treatment of the periodontal disease. Accordingly, in yet another embodiment of the invention, a method is provided for the treatment of periodontal disease affecting human gums surrounding the teeth. The method comprises heating a solid state periodontal medicament composition comprising (i) from 0.2 to 12.0 percent agar, (ii) from 1.25 to 10.0 percent povidone iodine, and optionally, (iii) up to 3 percent of a bio-compatible, radio-opaque salt that is opaque to X-rays or which can render the composition opaque, to a temperature of at least 180° F., preferably in a range of from 180° F. to 200° F., for at least 2 minutes, preferably from 6 to 10 minutes or more. The percentages expressed are based on the total volume of the composition, and preferences for the concentration ranges of the composition are the same as those stated for the preparation of the periodontal medicament composition described above. Heating the composition to the expressed temperatures and for the disclosed times is necessary to convert the composition to a liquid state. Thereafter, the resulting liquid medicament composition is lowered to a patient-receptive temperature range from 110° F. to 149° F., preferably from 110° F. to 140° F., followed by transporting the liquid composition to the area of the gums afflicted with periodontal disease. The afflicted area is defined as a periodontal pocket whose boundaries are typically designated by the space between the afflicted area of the human gums and the teeth. Once transported into the periodontal pocket, the liquid medicament composition is allowed to congeal whereupon a solid implant is formed in the pocket for the release of the povidone iodine into the pocket for treating the periodontal disease.

Another embodiment of the invention includes a prepackaged periodontal medicament delivery system for the treatment of periodontitis. The prepackaged system broadly includes a tubular dispensing apparatus, preferably a syringe, for retaining and storing in a solid state, a predetermined amount, preferably one or more treatment units, of the periodontal medicament composition described above, and for delivery of the composition, once converted to a liquid state, to the periodontal pocket of a patient afflicted with periodontal disease. The latter function of the delivery system is accommodated by the inclusion in the system of a funnel-shaped tubular device, preferably in the form of a cannula, that is adapted for coupling with the dispensing apparatus to facilitate the composition's delivery into the patient's periodontal pocket while in its liquid state. The amount of each treatment unit preferably comprises from 1 to 5 cc, and the capacity of the tubular dispensing device may be capable of retaining up to 30 cc of the periodontal medicament composition. For purposes of storage and shipping, the tubular dispensing apparatus and funnel shaped tubular device are packaged in a light-resistant container.

More specifically, the tubular dispensing apparatus comprises (i) a longitudinal tube having a receiving end and a dispensing end. The longitudinal tube contains a predetermined amount of the previously described periodontal medicament composition, i.e., one or more treatment units, in a solid state form. The dispensing apparatus also comprises (ii) a piston that has a dispensing end and an opposite delivery end. The piston is adapted for slidable insertion into the receiving end of the longitudinal tube for delivery of the medicament composition through the dispensing end of the tube after the medicament composition has been converted to a liquid state. A resilient material is disposed about the dispensing end of the piston that interfaces with the internal surface of the longitudinal tube to provide a slidable and sealable resistance fit as the piston is moved within the tube. The piston's movement within the tube is limited by the provision of a lateral stop disposed about the piston's delivery end when it butts against an annular stop provided about the receiving end of the longitudinal tube. This limited movement coincides with the medicament composition's complete dispensation from the longitudinal tube. A detachable end cap is fitted about the dispensing end of the longitudinal tube. It is removed and replaced by the funnel-shaped tubular device when the medicament composition, after conversion to its liquid state, is ready to be delivered into the patient's periodontal pocket.

It is understood that the tubular dispensing apparatus is capable of withstanding its subjection to the temperature changes necessary, as previously disclosed, for converting the medicament composition from its solid state to a liquid state and from a liquid state to a solid state.

DETAILED DESCRIPTION OF THE INVENTION AND PREFERRED EMBODIMENTS THEREOF

Figure 1:
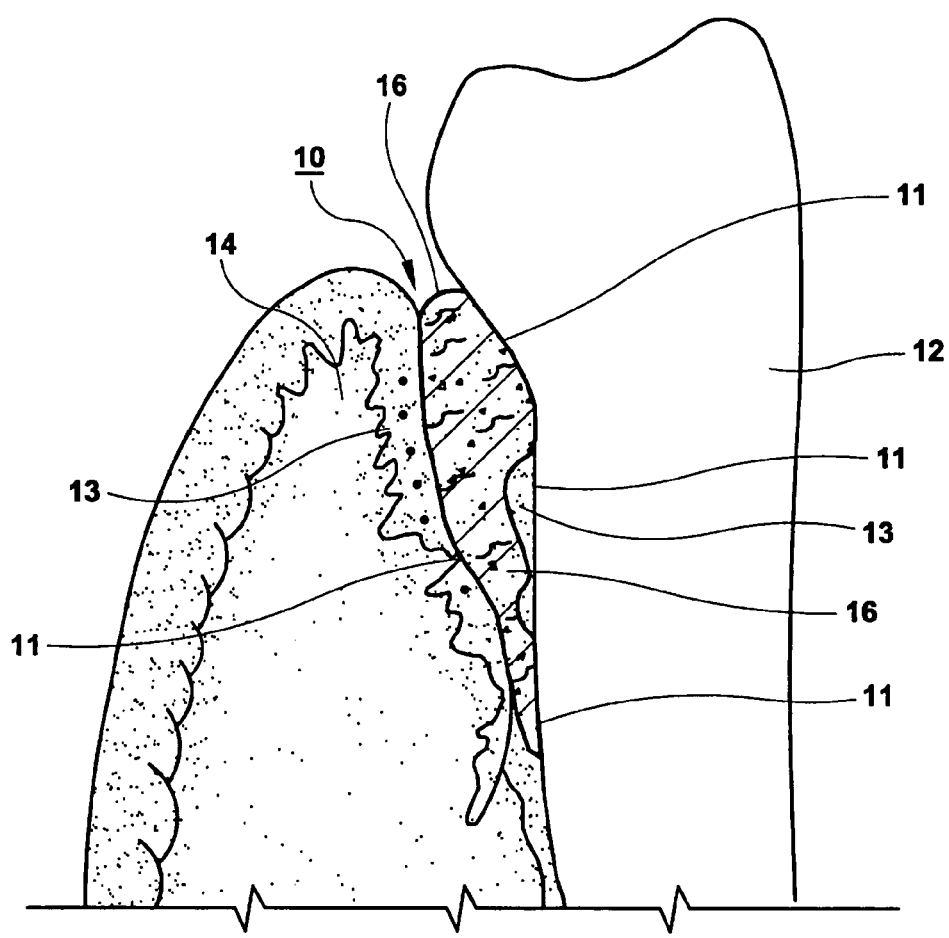
FIG. 1 is a cross-sectional plan view of the tissues and tooth surrounding a periodontal pocket in the mouth of a patient afflicted with periodontal disease.

In accordance with the invention, a periodontal medicament composition and method is provided for the treatment of periodontal disease. The periodontal composition comprises a medicament and a carrier such that when the composition is suitably prepared and liquified, it is capable of being introduced into the periodontal pocket of a patient suffering from periodontal disease to form a periodontal medicament implant in situ, and thereafter allow the sustained release of the medicament into the pocket for a sufficient period of time to effect the elimination of the disease-causing microbes from the pocket. The medicament is povidone iodine and the carrier is agar. The minimum period of time for the treatment of the disease is 24 hours, and is typically a period of 1-3 days in order to achieve maximum effectiveness. One distinct advantage of the periodontal composition for treating periodontal disease is that it is free of antibiotics and the potentially harmful and undesirable side effects that often accompany the use of antibiotics.

In order to accomplish this, the invention takes advantage of the reversible hydrocolloid properties of the substance agar. Agar (*Gelium mansli*) is a mucilaginous substance derived from several varieties of marine algae or seaweeds, as for example, *Gelidium corneum, Gracilaria lichenoides, Gigartina speciosa*. Insoluble in cold water, it swells to several times its original volume when dissolved in hot water, and maintains its structural integrity in moisture over a prolonged period of time. Moreover, its compatibility with povidone iodine lends itself for the twofold purpose of providing a carrier as well as a binding and release agent for a povidone iodine medicament.

Therefore, in accordance with one aspect of the invention, a periodontal composition is provided by combining povidone iodine with agar. The composition comprises from 1.2 to 10.0 percent of povidone iodine and from 0.2 to 12.0 percent agar, the percentages being based on the total volume of the composition. The periodontal composition is in a solid state form below 100° F. at the expressed concentration ranges. A concentration of agar above 12% by volume in the periodontal composition will render the composition difficult to handle because of the accompanying increased viscosity which contributes to an increased rigidity of the composition. A concentration of agar below 0.2% by volume of the composition will deprive the composition of its necessary elasticity and/or solidity for retaining the resulting medicament implant in the periodontal pocket.

The periodontal composition according to the invention is obtained by preparing a 0.2 to 2.0 percent by volume aqueous solution of agar, and then heating the solution to a temperature above 180° F., preferably in the range of from 180° F. to 200° F., for at least two minutes, preferably from 6 to 10 minutes or more. Thereafter, from 1.25 to 10.0 percent by volume of povidone iodine, based on the total volume of the resulting liquid periodontal composition, is added to the aqueous agar solution and is optionally stirred to ensure the homogeneity and translucency of the solution ingredients. Once the composition is formulated and liquified, it's temperature is lowered to room temperature whereupon it congeals into a solid state form for, by way of example, appropriate packaging into individual treatment units for future use, or into bulk form for purposes of storage and transport.

A sufficient amount of a radio-opaque salt may optionally be added to the composition at any time point in time during the composition's formulation. Adding a radio-opaque salt aids in the visualization of the placement of the resulting medicament implant in the periodontal pocket when X-rays are taken of the affected region of the mouth. Thus, the inclusion of a radio-opaque material in the periodontal medicament composition permits the resulting medicament implant to be quickly located for removal, monitoring, and the like. The radio-opaque material may include, or be formed of any suitable material, which is itself opaque to X-rays or can render the resulting medicament implant opaque. While not required, a bio-compatible and biodegradable material is preferred. For example, the radio-opaque material may include a radio-opaque non-toxic salt or oxide of a heavy metal atom, e.g., barium sulfate or barium sulfate monomer, tin methacrylate monomer, zirconium dioxide, bismuth trioxide, bismuth subcarbonate, zirconium dioxide, or simply tungsten. As a guideline for the amount of the radio-opaque salt in the composition, it should be in a concentration that will be non-toxic to the human body without any side effects and conform to levels that are compatible with EPA safety guidelines for the radio-opaque salts set forth above. Accordingly, the concentration of the radio-opaque material in the periodontal medicament composition may be present up to 3 percent, preferably from 0.1 to 1.0 percent, based on the total volume of the medicament composition.

The method for administering the periodontal medicament composition for the treatment of the periodontal disease involves several steps. Since the appropriate compositional makeup of the periodontal composition is in solid state form at room temperature, as well as at the internal temperature of the human mouth, it must be made suitable for transfer into the periodontal pocket in a manner that will conform to and be retained within the contours of the pocket. Typically, a single treatment, or treatment unit, of the periodontal composition will comprise from 1 to 5 cc., preferably 2 to 4 cc., and for purposes of being capable of treating more than one area of the mouth or the entire mouth, a single treatment can be sized approaching the upper volumetric range, i.e., from 4 to 5 cc. It will be understood that the amount of periodontal medicament composition to be administered to the periodontal pocket will vary depending on the circumstances of the infection, specifically the extent of the infection, the anatomical configuration of the pocket, and the size and/or depth of the pocket for treatment. In this regard, a maximum treatment unit or more than one treatment unit may be necessary if the periodontal disease has progressed to more than one area or larger areas of the gums.

The first step for the treatment of the periodontitis is undertaken by heating a treatment unit of the solid state composition to a temperature above 180° F., preferably to about 185° F., and generally in the range of from 180° F. to 200° F., for a short period of time, i.e., at least two minutes and preferably for 6 to 10 minutes or more, to insure homogeneity of the composition, whereupon, as previously stated, it is completely converted to a liquid solution. Heating and maintaining the composition at this temperature range can be undertaken by any conventional means, e.g., by means of a dry-heating or electric heating device with a thermostatically controlled unit for maintaining the composition at a constant temperature, e.g., an electric plate heater. It will be understood that the medicament composition can be heated to above its boiling temperature for converting it to a liquid state. However, heating the medicament composition to a significantly higher temperature above boiling for a sustained length of time can subject the composition to concentration alterations whereby the agar will no longer be effective as a carrier for the povidone iodine. This same caution applies when the periodontal medicament composition is being prepared.

Thereafter, the temperature of the liquid medicament composition is lowered to what is referred to as a "patient receptive temperature range," i.e., a temperature range at which the composition can be transferred, while in a liquid state, to the periodontal pocket of a patient afflicted with periodontal disease without serious discomfort to the patient or a burning of the gum tissues. This temperature range is 110° F. to 149° F., and is preferably from 110° F. to 140° F. The treatment unit is held within the patient receptive temperature range for as long as necessary until the treating healthcare provider is ready to transfer the liquid composition to the periodontal pocket of a patient's mouth. The stability of the medicament composition enables it to be sustained at this temperature range for as long as necessary. It will be understood that the composition can be in a liquid state at higher temperatures, but should not exceed 149° F. for the reasons just stated. In addition, a higher concentration range of agar will dictate a higher temperature within the patient receptive temperature range for manifesting the composition in a liquid state. Conversely, a lower concentration of agar will dictate maintaining the temperature of the periodontal composition at the lower end of the patient receptive temperature range. It should also be noted that the reversible hydrocolloid properties of agar for use as a carrier for the povidone iodine medicament advantageously enables the periodontal medicament composition to shift back and forth between a solid and liquid state without affecting the stability or effectiveness of the composition, or the capability of having the composition delivered to the infected periodontal pocket.

Figure 3:
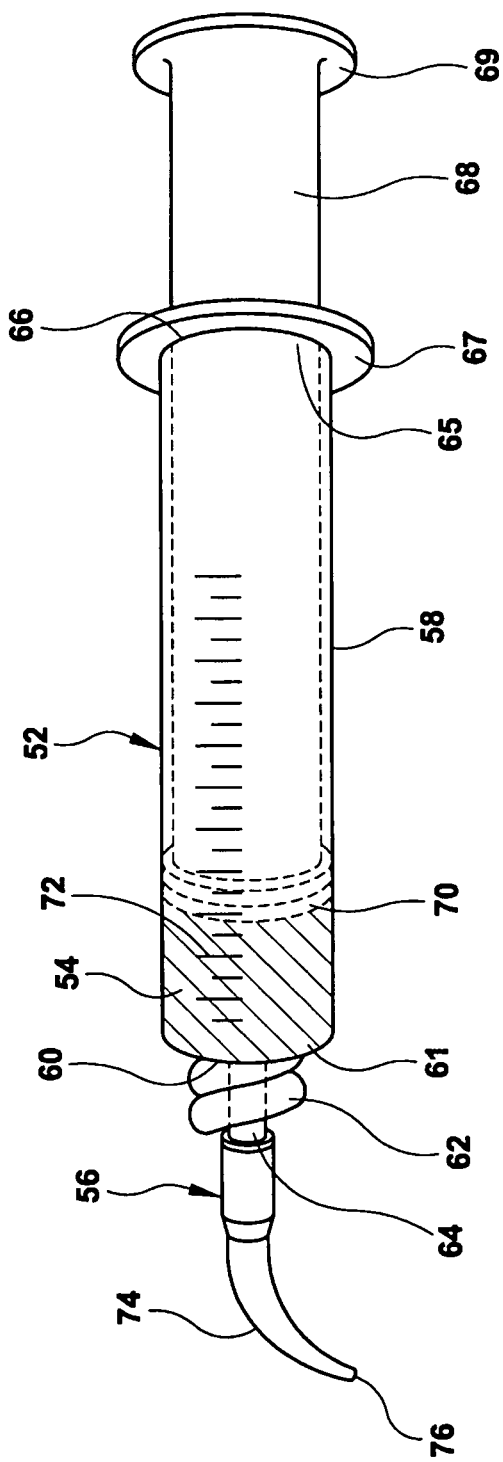
FIG. 3 is an elevated plan view showing the assembly of the individual parts of the prepackaged periodontal delivery system shown in FIG. 2 prior to injecting a periodontal medicament composition 54 in its liquid state into the periodontal pocket of a patient afflicted with periodontal disease.

While still maintaining the periodontal composition in its liquid state, it is transported into the periodontal pocket, preferably by the use of a tubular dispensing apparatus, e.g., an adequately sized syringe or one having a capacity of retaining up to 30 cc of the medicament composition, coupled with a cannula having a sufficiently large opening to permit injection of the medicament composition without causing premature congealing or solidification due to cooling (see FIG. 3). When withdrawing the liquid into its dispensing apparatus, caution should be taken to do so while the treatment unit is still within the patient receptive temperature range at which the liquid state is being maintained. If the temperature of the withdrawn liquid falls below the patient receptive temperature range, e.g., below 110° F., the liquid unit will start to congeal and become increasingly viscous owing to the temperature sensitive properties of the agar carrier. As the temperature lowers, its viscosity will increase to the point where it will be difficult to inject the medicament composition into the periodontal pocket. Furthermore, as its temperature approaches the internal temperature of the human mouth, generally below 100° F., transformation into a substantially solid state will occur.

Figure 2:
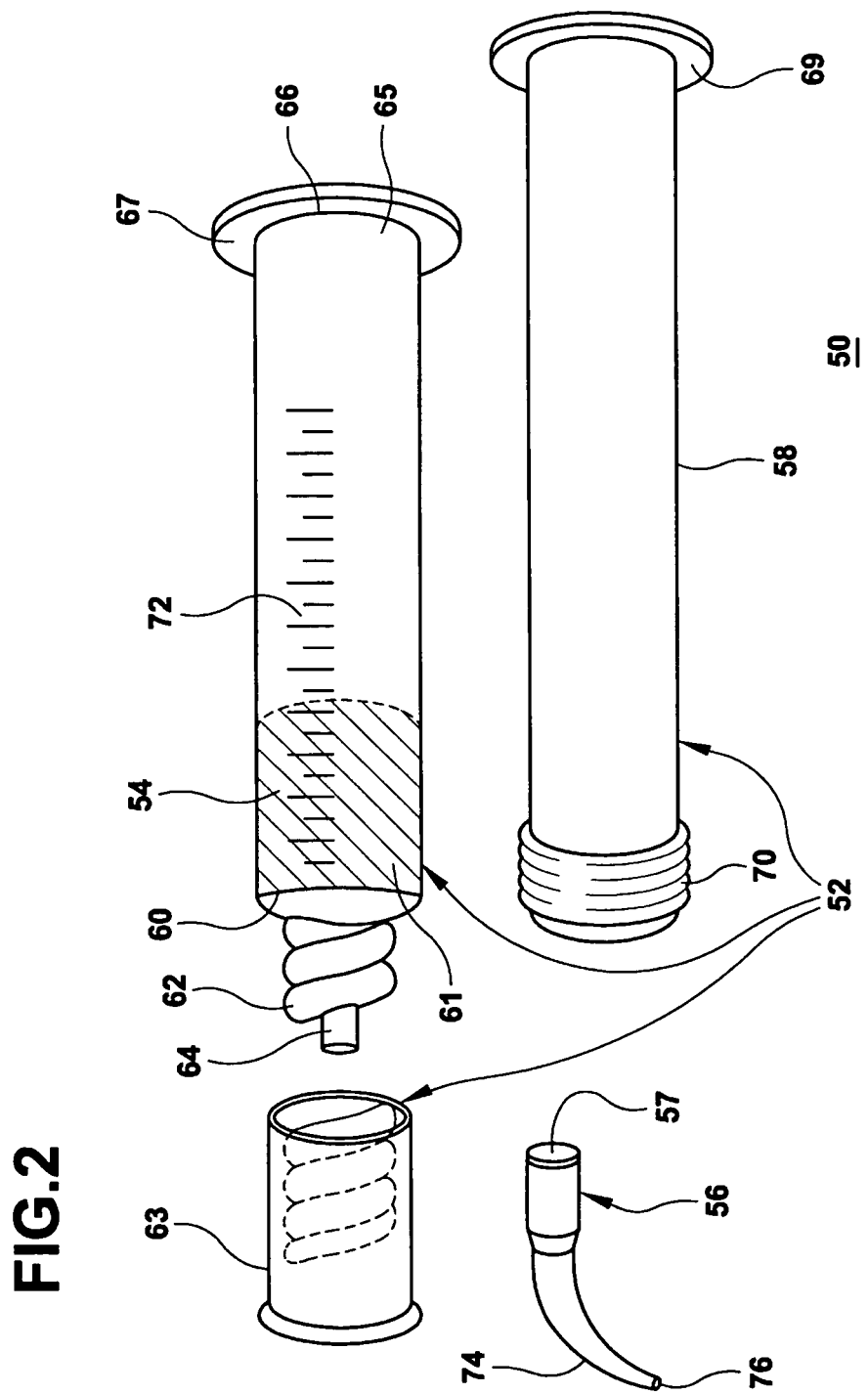
FIG. 2 is a perspective view of individual parts for assembly into a prepackaged delivery system for the treatment of periodontal disease.

Once withdrawn into an appropriate dispensing apparatus, e.g., such as the one illustrated in FIGS. 2-3, the withdrawn solution is injected into the periodontal pocket of the patient. After insertion into the periodontal pocket, whose temperature is typically in the range of 98-99° F., i.e., the average internal temperature of the mouth, the still-liquid treatment unit substantially fills the defining contours of the pocket and proceeds to cool to this temperature range. As the injected treatment unit cools to the internal temperature of the mouth, it congeals and reaches a point of substantial solidity in a relatively short period of time, usually from 1 to 3 minutes. In order to expedite the congealing of the treatment unit within the periodontal pocket, external cooling means can be applied to the jaw of the patient using an ice pak or simply by lavaging the mouth with cold water.

Upon reaching a sufficient degree of solidity, the composition is transformed into a periodontal medicament implant that obtains the shape and size of the periodontal pocket. By forming the implant in situ in accordance with the invention herein, its size and firmness will be sufficient to have the implant retained within the periodontal pocket. This insures that the peridone iodine medicament will be released within the pocket over a period of time for addressing the periodontitis. It will be understood that multiple pockets can be treated or filled from a dispensing apparatus with a single treatment unit using the same method depending on the size of the treatment unit.

The application of a treatment unit to a patient afflicted with periodontal disease is described in greater detail by reference to FIG. 1. A periodontal pocket 10 is illustrated which is formed between a tooth structure 12 and gum structure 14 of a patient afflicted with periodontal disease. The representation of diseased tissue is illustrated by reference number 13. FIG. 1 also illustrates a treatment unit according to the invention in the form of implant 16 positioned within pocket 10 after sufficient time has passed to allow for the treatment unit's substantial solidification. As illustrated, implant 16 substantially conforms to contoured surfaces 11. As such, contoured surfaces 11 of tooth structure 12 and gum structure 14 define and represent the periodontal pocket 10.

The substantial conformance of implant 16 to surfaces 11 of pocket 10 assists in the treatment of the disease in two regards. First, introduction of the treatment unit in its liquid state becomes optimally located within pocket 10 to release the povidone iodine medicament directly to the diseased tissue 13 formed within and on the contour surfaces 11 of pocket 10. Secondly, the liquid treatment unit, upon reaching a sufficient degree of solidity to form implant 16 according to the invention, is of a sufficient size and firmness that it will remain within pocket 10. This status is maintained until implant 16 becomes free of its own accord or is physically removed, e.g., by a professional healthcare provider. As such, implant 16 is retained within pocket 10 by virtually being held "captive" by the physical contours 11 of the pocket. During the effective period of treatment, i.e., the first several days, dislodging of the implant from pocket 10 is avoided by ordinary ingestion activities, such as with the consumption of or gargling with liquids, or the chewing and eating of food. Eventually, however, usually after several days, the implant 16 will work itself out of periodontal pocket 10 by the day-to-day mechanics of the movement of the mouth. If the pocket is deep enough, i.e., more than 7-8 mm, it may be necessary for the treating healthcare provider to manually remove implant 16.

Once implant 16 is formed in situ, the povidone iodine will be released over a period of time from the agar carrier due to the povidone iodine's solubility in and gravitation to the moist saliva within the mouth. This sustained release of the povidone iodine is induced by the aqueous exchange between the povidone iodine suspended in the agar carrier, and the moisture in the patient's mouth. This enables a gradual release of the povidone iodine into periodontal pocket 10. The exchange is evident and demonstrated by the in vitro studies set forth in the Examples herein.

Another advantage of using agar as the carrier for the periodontal composition is that it lacks substantial bio-adhesion to human tissue. For the purposes of describing the invention herein, by "bio-adhesion" is meant adhesion through chemical or mechanical integration (as by intergrowth) between implant 16 and the contour surfaces 11 of pocket 10. Implant 16 will therefore not adhere to the contour surfaces 11 of the pocket. With the implant lacking in bio-adhesion, the treating healthcare provider can remove it without difficulty as may be necessary after it has been in place for a longer than usual period of time; or as may be required if the injection of the periodontal medicament composition into pocket 10 was incomplete or improper; or if the patient exhibits an allergic reaction to the implant. This lack-of-adherence feature distinguishes over various prior art polymer-based carriers which bio-adhere to tissues and are difficult and painful to remove.

With the establishment of implant 16 in periodontal pocket 10, the povidone iodine is slowly released into the pocket for treating the periodontitis. The rate of release of the povidone iodine medicament from its agar carrier depends in large part upon the concentration of povidone iodine in the treatment unit, and to a lesser extent upon the agar concentration making up the treatment unit. While povidone iodine effectively and substantially kills periodontal disease-causing microbes, the use of the agar carrier in the manner defined herein permits small, non-toxic concentration ranges and amounts of povidone iodine to be released over a sustained period of time for treating the periodontitis which is confirmed by the tests set forth in the Examples that follow.

Since the periodontal medicament composition is in a relatively stable, solid state at room temperature, this property alone will allow it to be packaged, transported and stored for eventual administration by a treating healthcare provider to a person suffering from periodontal disease. Packaging a pre-prepared treatment unit, therefore, becomes desirable for a treating healthcare provider to administer the treatment unit in an efficient and effective manner. Thus, in another embodiment of the invention, units of the periodontal composition can be manufactured, sized and packaged for individual treatment units or administration doses. However, certain guidelines must be observed when packaging the periodontal medicament composition because of its temperature sensitivity and decomposition susceptibility when subjected to elevated temperatures and the influence of natural light, respectively. Therefore, care must be taken to store any packaging at room temperature or below, and any packaging of the final end product must be in a light-resistant package, e.g., tin foil, opaque plastics such as MYLAR®, STYROFOAM®, cardboard, or in any packaging material that will not allow the transmission of light therethrough.

Of particular benefit to a professional healthcare provider when administering the medicament composition is to have a pre-determined amount available in a dispensing apparatus that allows efficient delivery to the patient's periodontal pocket 10 illustrated in FIG. 1. Therefore, in accordance with another aspect of the invention, FIGS. 2 and 3 illustrate embodiments of a periodontal medicament delivery system 50 for effective and efficient administration of a periodontal medicament treatment unit 54. As best shown in FIG. 2, the delivery system 50 comprises a periodontal medicament dispensing apparatus 52 for retaining and storing a treatment unit 54, in this case, 3 cc of the periodontal medicament composition. A funnel-shaped tube 56 is also provided for replacing end cap 63 (see FIG. 3) when treatment unit 54 is ready to be delivered into the patient's periodontal pocket 10 (FIG. 1) while in a liquid state.

As shown in FIG. 2, dispensing apparatus 52 comprises a transparent or semi-opaque longitudinal tube 58 of a hardened plastic construction, a plunger 68, and a detachable, internally threaded, protective end cap 63. Longitudinal tube 58 has a dispensing opening 60 defined by dispensing end 61 at one end thereof, and a receipt opening 66 defined by receipt end 65 at its opposite end. Concentrically disposed about the dispensing end 61 of tube 58 is a relatively smaller tubular extension 62 that is threaded on its outer surface for receiving correspondingly threaded protective end cap 63 in fixed relationship to tubular extension 62. Within tubular extension 62 is a smaller concentric tubular male protrusion 64 configured in size and length for receiving the female opening 57 of funnel-shaped tube 56 with a slidable resistance fit. Protective end cap 63 is fixed to tubular extension 62 during storage and shipment of delivery system 50, and removed for replacement by funnel-shaped tube 56 when dispensing apparatus 52 is ready for the transport of treatment unit 54 into periodontal pocket 10.

At the opposite end of longitudinal tube 58, an annular stop 67 is provided about the outer circumference of receipt end 65. Receipt opening 66 at receipt end 65 is configured in size for slidably receiving therein a plunger 68. A bulb 70 is fitted about one end of plunger 68, bulb 70 being made of a pliable, resilient material, such as, for example, rubber or synthetic rubber, for interfacing with the internal surface of longitudinal tube 58. Bulb 70 serves as a slidable seal with the internal surface of tube 58 for retaining the contents of dispensing apparatus 52 therein, in this case treatment unit 54. The integration of bulb 70 with plunger 68 also provides the means for dispensing the treatment unit (in its liquid state) when plunger 68 is moved towards dispensing end 61. An annular stop 69 is provided about the outer circumference of the opposite end of plunger 68. The length of piston 68 is designed such that annular stop 69 will directly interface with annular stop 67 of longitudinal tube 58 when bulb 70 butts against the dispensing end 61 of longitudinal tube 58. In this way, all of the treatment unit 54, while in its liquid state, can be dispensed from apparatus 52. Along the external surface of longitudinal tube 58 are lined depictions 72 representing volumetric indications, in this case cubic centimeters, of the treatment unit 54 contained within dispensing apparatus 52. FIG. 2 shows 3 cc of treatment unit 54 in solid state form.

It will be understood that the individual parts that make up tubular dispensing apparatus 52 are of a construction that is capable of withstanding its subjection to temperature changes necessary, as previously described, for converting the medicament composition from its solid state to a liquid state and from a liquid state to a solid state.

As indicated above, longitudinal tube 58 of dispensing apparatus 52 contains a predetermined amount of treatment unit 54 which as illustrated in both FIGS. 2-3, is 3 cc's of the periodontal medicament composition formulated according to the description contained herein. When delivery system 50 is in storage or being shipped, treatment unit 54 is in solid state form, having been prepared and introduced into longitudinal tube 58 while in its liquid state and thereafter cooled to room temperature. Treatment unit 54 can be introduced into longitudinal tube 58 in any number of ways, one of which is to draw the liquid medicament composition into the tube by the use of plunger 68 (with protective end cap 63 removed). An alternative way is to introduce treatment unit 54 in its liquid state through receipt opening 66 of longitudinal tube 58 with plunger 68 removed. It will be understood that the size of dispensing apparatus 52 can be configured in size with a volumetric range of up to 30 cc for accepting the same amount of the periodontal medicament composition. However, it is preferable to configure the size of the dispensing apparatus to accept at least one or more treatment units of the periodontal medicament composition, each treatment unit preferably comprising, for example, from 1 to 5 cc's of the periodontal medicament composition. A syringe, e.g., a standard #54 syringe, is a preferred embodiment for use as the dispensing apparatus since it will accommodate a number of such treatment units for the treatment of a wide variety of periodontal conditions.

As shown in FIGS. 2-3, a funnel-shaped tube 56 is used to facilitate access to the periodontal pocket 10 illustrated in FIG. 1. Tube 56, which is preferably in the form of a cannula, can be of a plastic or metal construction. It has a curved section 74 that tapers to a narrow outlet opening 76 which is designed for easy access to the periodontal pocket. Female inlet opening 57 of funnel-shaped tube 56 is sized to accommodate the receipt of tubular male protrusion 64 with a removable resistance fit when protective end cap 63 is removed from longitudinal tube 58. The purpose of using a funnel-shaped tube as part of the periodontal medicament dispensing system 50 is to deliver the treatment unit 54 into the periodontal pocket illustrated in FIG. 1 without penetrating or puncturing gum tissue. The further advantage is that it allows delivery of the treatment unit 54 of the periodontal medicament composition into the pocket 10 as quickly as possible without incurring premature solidification or thickening of the medicament composition due to cooling caused by ambient conditions and/or the internal temperature of the patient's mouth. If this happens, in either longitudinal tube 58 or funnel-shaped tube 56, the delivery procedure will be totally or partially interrupted for failure of all or part of the medicament composition to reach the pocket. If a partial delivery of the medicament composition to the pocket occurs, an evaluation by the treating healthcare provider will have to be made whether re-application of the medicament composition is required. As a preference, a 16 to 24 gage cannula available from OraTech LLC of Salt Lake City, Utah, can be used, desirably an 18-22 gage cannula or a "bent mini delivery tip" cannula with the assigned numbers "10826" or "10899." Similar gaged Cannulas are also available from Ultradent Products, Inc., of South Jordan, Utah.

The periodontal medicament dispensing system 50 is assembled by first preparing the periodontal medicament composition according to the guidelines set forth hereinbefore. Once the composition is prepared and finalized at the elevated temperature of at least 180° F. for a period of at least 2 minutes, desirably for at least 6 minutes, the liquid medicament composition is ready for insertion into the periodontal medicament dispensing apparatus 52. The composition can be added to dispensing apparatus 52 at any temperature that will insure its liquidity while being deposited into the dispensing apparatus. This would include the patient receptive temperature range for ease of handling. Therefore, while the periodontal medicament composition is in its liquid state, one method is to have plunger 68 withdrawn from dispensing apparatus 52 and one or more treatment units of the liquid medicament composition can be introduced into longitudinal tube 58 via receipt opening 66 by any means that will effectively accomplish filling the longitudinal tube to its desired level. During this step, end cap 63 is fixed in place to tubular extension 62 of the dispensing apparatus. Once the liquid composition solidifies in the dispensing apparatus, plunger 68 is re-inserted into longitudinal tube 58 whereupon dispensing apparatus 52 can be packaged, shipped or stored in a light-resistant container along with funnel-shaped tube 56.

Another method for filling longitudinal tube 58 is to remove protective end cap 63 from the dispensing apparatus 58, whereupon plunger 68 can then be used to draw up the liquid periodontal medicament composition directly into the longitudinal tube until the desired amount of treatment unit 54 is reached. After the treatment unit has cooled into a solid state within longitudinal tube 58, protective end cap 63 is re-fitted back to dispensing apparatus 52. The resulting dispensing apparatus 52 and funnel-shaped tube 56 forms the periodontal medicament delivery system 50 which, as indicated above, is available for packaging in a light-resistant container and subsequent transport to a professional healthcare provider.

When the periodontal medicament treatment unit 54 contained within dispensing apparatus 52 is ready to be transported to the patient's periodontal pocket 10 by the treating healthcare provider, dispensing apparatus 52, with the protective end cap 63 in place, is heated to a temperature for converting the solid periodontal medicament treatment unit 54 to a liquid state, i.e., to at least 180° F., preferably from 180° F. to 200° F., for at least 2 minutes, preferably from 6 to 10 minutes or more. Once converted to the liquid state, the temperature of the periodontal medicament treatment unit 54 is lowered to the patient receptive temperature range of from 110° F. to 149° F., preferably from 110° F. to 140° F., and maintained as a liquid within this range until it is ready for transport into the periodontal pocket 10 of the subject patient. Heating and maintaining the composition within these temperature ranges can be undertaken by any conventional means, e.g., by means of a dry-heating or electric heating device with a thermostatically controlled unit for raising, lowering and/or maintaining the treatment unit at a constant temperature. In this type of heater, referred to as an "impression heater," the periodontal medicament dispensing apparatus 52 is inserted into an accommodating cylindrical receptacle for heating and maintaining the temperature of the treatment unit as just described above. An example of this type of heating apparatus is available from Cadco Products, Inc. as "Cadco Dry Processor li Ea Model 25310."

When the professional healthcare provider is ready to administer the treatment unit 54 to the periodontal pocket of the patient, dispensing apparatus 52 is removed from the impression heater (which has maintained the liquid treatment unit 54 within the patient receptive temperature range). End cap 63 is then quickly replaced with funnel-shaped tube 56 by attaching tube 56 to tubular male protrusion 64 of dispensing apparatus 52. The dispensing apparatus with the funnel-shaped tube 56 attached is fully illustrated in FIG. 3. Liquid treatment unit 54 is then injected into the periodontal pocket 10 of the afflicted patient (see FIG. 1) by depressing plunger 68. The liquid treatment unit is then allowed to cool to the internal temperature of the patient's mouth with the result that a substantially solid periodontal implant 16 is predominantly formed within the contours 11 of pocket 10. As described, the periodontal medicament delivery system allows the healthcare provider to completely transport one or more treatment units 54 into a periodontal pocket in an efficient manner which minimizes any premature gelling or solidification of the liquid medicament composition prior to its entry into the pocket. In this way, a periodontal medicament implant can be formed within the periodontal pocket leading to maximum treatment of the periodontal disease.

Throughout the disclosure that follows, the invention herein is augmented by means of exemplary embodiments which are intended as examples rather than limitations on the composition and methods according to the invention described herein. All parts and concentrations are by volume unless expressly stated otherwise.

The following examples describe and demonstrate the effectiveness of agar carriers containing povidone iodine over a range of concentrations against a known microorganism *S. mutans* ATCC 25175 that is prevalent with periodontal disease.

Example 1

The following describes the preparation of carriers containing various aqueous concentrations of agar.

A 02% agar carrier was prepared by weighing 0.1 grams of agar and dissolving it into 50 ml of water to produce an aqueous solution of 0.2% agar. The mixture was made soluble by subjecting it to steamed heat under pressure in an autoclave. Thereafter, the agar solution was allowed to cool to room temperature whereupon it congealed into a solid state form to provide the 0.2% agar carrier.

Examples 2-3

Carriers containing 2.0% and 12% agar were also prepared under the same conditions set forth in Example 1, i.e., by dissolving 1.0 grams and 6.0 grams of agar, respectively, in 50 ml of water to provide a 2.0% agar carrier (Example 2) and a 12% agar carrier (Example 3).

Examples 4-6 describe the preparation of periodontal compositions using 10% aqueous concentrations of povidone iodine.

Example 4

A periodontal composition comprising an aqueous solution of 0.2% agar and 10% povidone iodine was prepared by mixing 0.05 grams of agar and 25 grams of povidone iodine in an appropriate amount of water, followed by heating the solution to boiling to achieve solution of the mixture. The aqueous solution was allowed to cool to room temperature whereupon it congealed into a solid state form to provide a 0.2%/10% agar/povidone iodine periodontal composition, the balance of the composition being water.

Example 5

A periodontal composition comprising 2.0% agar and 10% povidone iodine was prepared in the same manner set forth in Example 4 using 0.2 grams of agar and 10 grams of povidone iodine.

Example 6

A periodontal composition comprising 12.0% agar and 10% povidone iodine was prepared in the same manner set forth in Example 4 using 1.2 grams of agar and 10 grams of povidone iodine.

In order to test the effectiveness of the agar/povidone iodine periodontal compositions prepared according to Examples 4-6 against disease causing microorganisms, the following compositions were prepared (described under Examples 7-8) for testing the periodontal compositions in a test plate.

Example 7

Brain heart infusion (BHI) agar, available from the manufacturer Oxoid Limited, was prepared by suspending 47 grams of BHI agar into one liter of water, boiling the mixture to dissolve the medium completely, dividing the solution into appropriate containers, and thereafter allowing the BHI agar to cool to room temperature to produce BHI agar samples in a solid-state form.

Example 8

A microorganism sample was prepared by plating *S. mutans* ATCC (American Type Culture Collection) 25175 on the BHI agar sample followed by incubation at 35-37° C. for 18-24 hours in a $CO_2$-enriched atmosphere. Organisms on this plate were then used to create a McFarland 0.5 suspension (approximately $1.5 \times 10^8$ CFU/ml) of the microorganism in sterile saline.

A microorganism test plate was then prepared by taking the BHI agar and placing it in a boiling water bath for conversion to liquid state. Following liquefication, the BHI agar was placed into a bath at 45° C., and incubated for approximately 60 minutes. A $\frac{1}{100}$ dilution of a McFarland 0.5 suspension of the microorganism was prepared, and 1.0 ml was added to a petri dish. Approximately 15 ml of the incubated BHI agar were poured into the petri dish at room temperature and allowed to harden. Using a ⅜-inch sterile hole punch, 10 holes were cut into the microorganism-containing BHI agar. The resulting BHI agar plugs were then removed leaving the holes for the insertion of various samples of the periodontal medicament compositions to determine their effectiveness against the microorganisms contained in the BHI agar.

Test 1

A 0.2% solidified agar sample prepared according to Example 1 was converted into a liquid state by its placement in a 65° C. water bath. The 0.2% agar sample was then used to prepare ½, ¼ and ⅛ dilutions of the 0.2% agar/10% povidone iodine periodontal composition prepared according to Example 4. Two samples of the various dilutions, i.e., undiluted, ½, ¼, and ⅛, were pipetted into the individual holes placed in the microorganism-containing BHI agar of Example 8. Two samples of the 0.2% agar without povidone iodine were also pipetted into individual holes of the microorganism-containing BHI agar to serve as controls.

The microorganism-containing BHI agar plate was then incubated at room temperature for approximately 30 minutes in order to allow the multi-diluted periodontal medicament composition samples to harden into plugs. The microorganism-containing BHI agar plate was then incubated in a $CO_2$-enriched environment for 24-28 hours. Thereafter, the plate was visually inspected for growth and the diameters of the zones of inhibition surrounding the 0.2% agar samples and variously diluted 0.2% agar/10% povidone iodine samples were measured. The greater the diameter surrounding the test sample, the more effective the test sample was for inhibiting growth of the microorganism. The visual inspection results of Test 1 are shown in Table 1.

TABLE 1

Zones of inhibition of the microorganism were observed around all of the variously diluted plugs containing the 0.2% agar/10% povidone iodine periodontal composition samples.

| 0.2% Agar/ 10% Povidone Iodine Plug | Diameter of the Zone Surrounding the Plug (mm) | Average Diameter Size (mm) |
| --- | --- | --- |
| Undiluted | 14.5 and 12.3 | 13.4 |
| ½ Dilution | 11.5 and 11.3 | 11.4 |
| ¼ Dilution | 9.7 and 9.7 | 9.7 |
| ⅛ Dilution | 8.2 and 8.2 | 8.2 |
| Control (no medicament) | No inhibition | — |

Test 2

A 2.0% solidified agar sample prepared according to Example 2 was converted into a liquid state by its placement in a 55° C. water bath. The 2.0% agar sample was then used to prepare ½, ¼ and ⅛ dilutions of the 2.0% agar/10% povidone iodine periodontal composition prepared according to Example 5. Two samples of the various dilutions, i.e., undiluted, ½, ¼, and ⅛, were pipetted into the individual holes placed in a microorganism-containing BHI agar plate prepared according to Example 8. Two samples of the 2.0% agar without povidone iodine were also pipetted into individual holes of the microorganism-containing BHI agar to serve as controls.

The microorganism-containing BHI agar plate was then incubated at room temperature for approximately 30 minutes in order to allow the multi-diluted periodontal compositions to harden into circular plugs. The microorganism-containing BHI agar plate was then incubated in a $CO_2$-enriched environment for 24-28 hours. Thereafter, the plate was visually inspected for growth and the diameters of the zones of inhibition surrounding the 2.0% agar samples and variously diluted 2.0% agar/10% povidone iodine samples were measured. As in Test 1, the greater the diameter surrounding the test sample, the more effective the test sample was for inhibiting growth of the microorganism. The visual inspection results of Test 2 are shown in Table 2.

TABLE 2

| 2.0% Agar/ 10% Povidone Iodine Plug | Diameter of the Zone Surrounding the Plug (mm) | Average Diameter Size (mm) |
| --- | --- | --- |
| Undiluted | 15.1 and 15.1 | 15.1 |
| ½ Dilution | 11.6 and 10.1 | 10.9 |
| ¼ Dilution | 9.0 and 9.0 | 9.0 |
| ⅛ Dilution | 8.2 and 8.2 | 8.2 |
| Control (no medicament) | No inhibition | — |

Test 3

A 12.0% solidified agar sample prepared according to Example 3 was converted into a liquid state by its placement in a 65° C. water bath. The 12.0% agar sample was then used to prepare a ½ dilution of the 12.0% agar/10% povidone iodine periodontal composition prepared according to Example 6. Four samples of the undiluted 12.0% agar/10% povidone iodine concentrations and two samples of the ½ dilution sample were pipetted into the individual holes placed in a microorganism-containing BHI agar plate prepared according to Example 8. Two samples of the 12.0% agar without povidone iodine were also pipetted into individual holes of the microorganism-containing BHI agar to serve as controls.

The microorganism-containing BHI agar plate was then incubated at room temperature for approximately 30 minutes in order to allow the multi-diluted medicament-containing agar samples to harden into circular plugs. The microorganism-containing BHI agar plate was then incubated in a $CO_2$-enriched environment for 24-28 hours. Thereafter, the plate was visually inspected for growth and the diameters of the zones of inhibition surrounding the 12.0% agar samples and variously diluted 12.0% agar/10% povidone iodine periodontal compositions were measured. As in Test 1, the greater the diameter surrounding the test sample, the more effective the test sample was for inhibiting growth of the microorganism. The visual inspection results of Test 3 are shown in Table 3 below.

TABLE 3

| 12.0% Agar/ 10% Povidone Iodine Plug | Diameter of the Zone Surrounding the Plug (mm) | Average Diameter Size (mm) |
| --- | --- | --- |
| Undiluted | 17.9 and 18.9 | 18.4 |
| Undiluted | 23.2 and 23.2 | 23.2 |
| ½ Dilution | 10.6 and 10.6 | 10.6 |
| Control (no medicament) | No inhibition | — |

In order to ascertain the stability of the periodontal compositions, the following tests were run for a 2%/10% agar/povidone iodine composition to observe its activity against a microorganism-containing BHI agar plate for a period of 1-2 days, and also for a period of 14 days at varying incubation temperatures.

Test 4

Once again, a 2.0% solidified agar sample prepared according to Example 2 was converted into a liquid state by its placement in a 45° C. water bath. The 2.0% agar sample was then used to prepare ½, ¼ and ⅛ dilutions of a 2.0% agar/10% povidone iodine periodontal composition that was prepared according to Example 5. Two samples of each of the various dilutions, i.e., undiluted, ½, ¼, and ⅛, were pipetted into the individual holes placed in a microorganism-containing BHI agar plate prepared according to Example 8. Two samples of the 2.0% agar without povidone iodine were also pipetted into individual holes of the microorganism-containing BHI agar to serve as controls.

The microorganism-containing BHI agar plate was then incubated at room temperature for approximately 30 minutes in order to allow the multi-diluted periodontal compositions to harden into circular plugs. The microorganism-containing BHI agar plate was then incubated in a $CO_2$-enriched environment for 24-28 hours. Thereafter, the plate was visually inspected for growth and the diameters of the zones of inhibition surrounding the 2.0% agar samples and variously diluted 2.0% agar/10% povidone iodine samples were measured. As in Test 2, the greater the diameter surrounding the test sample, the more effective the test sample was for inhibiting growth of the microorganism. The visual inspection results of Test 4 are shown in Table 4.

TABLE 4

| 2.0% Agar/ 10% Povidone Iodine Plug | Diameter of the Zone Surrounding the Plug (mm) | Average Diameter Size (mm) |
|---|---|---|
| Undiluted | 13.5 and 12.5 | 13.0 |
| ½ Dilution | 11.9 and 11.9 | 11.9 |
| ¼ Dilution | 10.0 and 10.4 | 10.2 |
| ⅛ Dilution | 8.9 and 8.7 | 8.8 |
| Control (no medicament) | No inhibition | — |

Samples of each dilution of the 2%/10% agar/povidone iodine and their incorporation into corresponding BHI agar plates as described in Test 4, were incubated at 4-8° C., 20-25° C., and 35-37° C., and stored for 14 days. Thereafter, the zones of each test plate was observed for diameter size which are summarized below.

| Incubation At 35-37° C. After 14 Days | | |
|---|---|---|
| 2.0% Agar/ 10% Povidone Iodine Plug | Diameter of the Zone Surrounding the Plug (mm) | Average Diameter Size (mm) |
| Undiluted | 10.5 and 10.3 | 10.4 |
| ½ Dilution | 7.4 and 7.4 | 7.4 |
| ¼ Dilution | 6.7 and 7.1 | 6.9 |
| ⅛ Dilution | 6.4 and 6.4 | 6.4 |
| Control (no medicament) | No inhibition | |

| Incubation At 20-25° C. After 14 Days | | |
|---|---|---|
| 2.0% Agar/ 10% Povidone Iodine Plug | Diameter of the Zone Surrounding the Plug (mm) | Average Diameter Size (mm) |
| Undiluted | 10.1 and 10.1 | 10.1 |
| ½ Dilution | 8.4 and 7.6 | 8.0 |
| ¼ Dilution | 7.6 and 6.8 | 7.2 |
| ⅛ Dilution | 6.2 and 6.2 | 6.2 |
| Control (no medicament) | No inhibition | |

| Incubation At 4-8° C. After 14 Days | | |
|---|---|---|
| 2.0% Agar/ 10% Povidone Iodine Plug | Diameter of the Zone Surrounding the Plug (mm) | Average Diameter Size (mm) |
| Undiluted | 8.7 and 8.7 | 8.7 |
| ½ Dilution | 7.8 and 8.0 | 7.9 |
| ¼ Dilution | 6.8 and 6.4 | 6.6 |
| ⅛ Dilution | 5.8 and 5.8 | 5.8 |
| Control (no medicament) | No inhibition | |

The above tests demonstrate the stability of the periodontal compositions at three different temperature ranges for a period of 14 days. From these examples and tests, it was determined that the periodontal compositions described therein were effective against micro-organisms that cause periodontal disease and can be used for the effective treatment of the disease over a sustained period of time in view of their stability and effectiveness over a wide range of temperatures.

The compositions and methods according to the invention, as demonstrated by the foregoing examples and written description, provide an effective treatment for periodontal disease without the deleterious effects and risks associated with lavaging the periodontal pocket with high concentrations of povidone iodine. At the same time, a useful and efficient periodontal product and prepackaged delivery system is provided that can be easily stored and retrieved in order to treat patients afflicted with periodontal disease without the risk associated with the use of toxic amounts of a povidone iodine medicament.

What is claimed is:

1. A method for the treatment of periodontal disease affecting human gums surrounding the teeth, comprising the steps of:
    a) heating a solid state periodontal medicament composition to a temperature of at least 180° F., said composition comprising
        i) from 1.25 to 10.0 percent povidone iodine by volume of the composition;
        ii) from 0.2 to 12.0 percent agar by volume of the composition, the agar being a carrier for said povidone iodine; and
        iii) optionally, up to 3 percent of a bio-compatible, radio-opaque salt by volume of the composition, the salt being opaque to X-rays or which can render the composition opaque;
    b) maintaining the temperature of the liquid medicament composition in step (a) above 180° F. for conversion of the medicament composition to a liquid state;
    c) thereafter lowering the temperature of the liquid medicament composition of step (b) to a temperature below 149° F. sufficient to maintain the medicament composition in a substantially liquid state;
    d) substantially filling a periodontal pocket of a patient with the liquid medicament composition, the pocket being defined as existing between contoured surfaces of gum structure and adjacent tooth structure; and
    e) allowing said composition to congeal into a substantially solid implant that is of sufficient size and that substantially conforms to the contoured surfaces so as to remain in the periodontal pocket for a sustained period of time of at least one day, wherein an aqueous exchange occurs between the povidone iodine suspended in the implant and moist saliva within the patient's mouth inducing the release of povidone iodine into the periodontal pocket over the sustained period of time.

2. The method according to 1, wherein the povidone iodine is present in an amount from 2 to 5 percent.

3. The method according to claim 1, wherein the agar is present in an amount from 5 to 10 percent.

4. The method according to claim 1, wherein the radio-opaque salt is a non-toxic salt or oxide of a heavy metal atom.

5. The method according to claim 4, wherein the radio-opaque salt is barium sulfate, barium sulfate monomer, tin methyacrylate monomer, zirconium dioxide, bismuth trioxide, bismuth subcarbonate or tungsten.

6. The method according to claim 4, wherein the radio-opaque salt is barium sulfate or barium sulfate monomer.

7. The method according to claim 1, wherein the radio-opaque salt is present in an amount from 0.1 percent to 1.0 percent.

8. The method according to claim 1, wherein the composition in step (b) is maintained at a temperature range from above 180° F. to 200° F. for at least two minutes.

9. The method according to claim 1, wherein the composition in step (c) is lowered to a patient-receptive temperature range from 110° F. to below 149° F.

10. The method according to claim 9, wherein the temperature range is from 110° F. to 140° F.

11. The method according to claim 1, wherein the method reduces the size of the periodontal pocket caused by a periodontal infection.

12. The method according to claim 1, wherein the method substantially eliminates bacteria in the periodontal pocket that causes the periodontal disease as well as decreasing microbial flora.

13. The method of claim 1, wherein the method increases attachment of the affected gum or gums to the tooth or teeth of the patient.

* * * * *